(12) United States Patent
Kim et al.

(10) Patent No.: US 9,186,797 B2
(45) Date of Patent: Nov. 17, 2015

(54) FORCE SENSING APPARATUS AND ROBOT ARM INCLUDING THE SAME

(75) Inventors: Jun-hyung Kim, Yongin-si (KR);
Hyun-do Choi, Yongin-si (KR);
Yeon-ho Kim, Hwaseong-si (KR);
Chang-bae Park, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 354 days.

(21) Appl. No.: 13/452,071

(22) Filed: Apr. 20, 2012

(65) Prior Publication Data
US 2013/0104672 A1 May 2, 2013

(30) Foreign Application Priority Data
Oct. 31, 2011 (KR) .......................... 10-2011-0112498

(51) Int. Cl.
*G01L 1/24* (2006.01)
*B25J 13/08* (2006.01)
*G01L 5/16* (2006.01)
*A61B 19/00* (2006.01)

(52) U.S. Cl.
CPC ........... *B25J 13/085* (2013.01); *A61B 19/2203* (2013.01); *G01L 1/246* (2013.01); *G01L 5/166* (2013.01); *A61B 2019/464* (2013.01)

(58) Field of Classification Search
None
See application file for complete search history.

(56) References Cited

U.S. PATENT DOCUMENTS

| 2006/0015021 | A1* | 1/2006 | Cheng .......................... 600/310 |
| 2008/0009750 | A1  | 1/2008 | Aeby et al. |
| 2009/0177095 | A1* | 7/2009 | Aeby et al. .................... 600/478 |
| 2010/0313679 | A1  | 12/2010 | Larkin et al. |

FOREIGN PATENT DOCUMENTS

KR 10-2008-0089582 10/2008

OTHER PUBLICATIONS

Jan Peirs et al., "A micro optical force sensor for force feedback during minimally invasive robotic surgery", Sensors and Actuators, 2004, pp. 447-455.
Ulrich Seibold et al., "Prototypic force feedback instrument for minimally invasive robotic surgery", *Medical Robotics*, 2007, 26 pages.

\* cited by examiner

*Primary Examiner* — Lisa Caputo
*Assistant Examiner* — Brandi N Hopkins
(74) *Attorney, Agent, or Firm* — Harness, Dickey & Pierce, PLC (57) ABSTRACT

A multi-axis force sensing apparatus that is installed at an operational end of a surgery robot and is capable of measuring force acting upon the operational end and a robot arm including the force sensing apparatus includes a body that is elastically deformable and has a pipe form extending along an axial direction of the body, an optical fiber strain gauge attached to a surface of the body to measure a tension and compression of the body in at least three directions. The optical fiber strain gauge may include at least three fiber Bragg gratings (FBGs) that are attached to the surface of the body and extended in an axial direction of the body, a light source providing light to each of the FBGs, and a light detector detecting light reflected by the FBGs or light that has passed through the FBGs.

22 Claims, 6 Drawing Sheets

FORCE SENSING APPARATUS AND ROBOT ARM INCLUDING THE SAME

CROSS-REFERENCE TO RELATED APPLICATIONS

This application claims the priority benefit of Korean Patent Application No. 10-2011-0112498, filed on Oct. 31, 2011, in the Korean Intellectual Property Office, the disclosure of which is incorporated herein in its entirety by reference.

BACKGROUND

1. Field

The following description relates to a force sensing apparatus and a robot arm including the same, and more particularly, to a force sensing apparatus, such as a force sensing apparatus installed at an operational end of a robot arm in order to measure forces acting on the operational end of the robot arm (particularly, a three-axis force sensing apparatus capable of sensing forces of three or more degrees of freedom), and a robot arm, such as a surgery robot arm, for example, including the force sensing apparatus.

2. Description of the Related Art

Robots for diverse uses have been developed and commercialized in line with the advances in robot technology. For example, a remote-controlled surgery robot connected to a surgical part of a patient assists a surgeon in conveniently conducting minute surgical operations by viewing the surgical part remotely via an endoscope screen. When using the surgery robot, hand shake caused as the surgeon moves his or her hand may be compensated for, and a remote surgical arm may reproduce a scaled-down motion of the surgeon's hand, and thus, precise operations may be conducted.

However, currently commercialized surgery robots provide only image information about a surgical part via an endoscope, and touch information, which can be obtained in general surgical operations, is not provided. That is, compared to a surgical operation actually performed using the hands, it is difficult for a surgeon to accurately figure out the amount of force applied to a surgical part by a surgical instrument attached to a surgery robot arm. Thus, if information about the intensity of a contact between the surgical instrument attached to the surgery robot arm and the surgical part is provided to the surgeon, the information about the contact, together with the image information, may be helpful for minute operations needed for cutting, cauterization, or suture, for example, of the surgical part. To this end, it is important to accurately measure forces acting between the surgical instrument attached to the surgery robot arm and the surgical part.

Accordingly, installment of a delicate force sensing apparatus at an operational end of a surgery robot has been researched. However, currently suggested force sensing apparatuses are not capable of accurately measuring forces in each direction, it is difficult to mount force sensing apparatuses on an arm portion of a surgery robot in a limited space, or such force sensing apparatuses may malfunction in an environment where a strong electromagnetic field exists. In addition, the range of forces measurable by the currently suggested force sensing apparatuses is relatively small.

SUMMARY

The following description relates to a force sensing apparatus for accurately measuring forces on more than three axes without being affected by an electromagnetic field, wherein the range of measurable forces is increased.

The following description relates to a robot arm including the force sensing apparatus.

Additional aspects will be set forth in part in the description which follows and, in part, will be apparent from the description, or may be learned by practice of the presented embodiments.

According to an aspect, a force sensing apparatus includes a body that is elastically deformable and has a pipe form extending along an axial direction of the body, at least three fiber Bragg gratings (FBGs) attached to a surface of the body, a light source providing light to each of the FBGs, and a light detector detecting light reflected by each of the FBGs or light that has passed through each of the FBGs.

The at least three FBGs may be arranged to extend along the axial direction of the body.

The at least three FBGs may be attached to the surface of the body in at least three different positions at predetermined intervals along an azimuth angle direction.

The FBGs may be attached to an external surface or an inner surface of the body.

The force sensing apparatus may further include at least three openings that are formed in the body between each two adjacent FBGs.

The body may be formed of a plastic material.

The force sensing apparatus may further include a plurality of bolt holes respectively formed in an upper portion and a lower portion of the body, An extension line between a center of the bolt holes and a center of the openings may be formed at a 45 degree angle with respect to a horizontal surface.

When an operational end of the force sensing apparatus is assumed to be an upper portion of the body, a center of the openings may be at a position lower than a center of the FBGs between each two adjacent FBGs.

The body may include an upper portion and a lower portion separated from each other, at least three elastic beams that connect the upper portion and the lower portion of the body and are extended in a direction perpendicular to an axis of the body, and gaps respectively formed between one of the elastic beams and the upper portion of the body and between one of the elastic beams and the lower portion of the body.

The body may be formed of a metal.

A first end portion of the elastic beam may be connected to the upper portion of the body, and a second end portion of the elastic beam disposed opposite to the first end portion may be connected to the lower portion of the body.

The body may further include at least three stoppers respectively formed between each two adjacent elastic beams.

The stopper may include a first protrusion that protrudes and extends from the lower portion of the body toward the upper portion of the body in the axial direction of the body; and a second protrusion that protrudes and extends from the upper portion of the body toward the lower portion of the body in the axial direction of the body to surround the first protrusion.

The first protrusion may include an intermediate portion having a relatively small width and an end portion having a relatively large width, and the second protrusion may include an intermediate portion having a relatively small width and an end portion having a relatively large width, wherein the first protrusion and the second protrusion are engaged with each other in a complementary form.

The gaps may extend between the first protrusion and the second protrusion.

The at least three elastic beams and the at least three stoppers may be formed in a monolithic manner by forming at least three gaps in the body by using a wire electrical discharge machining (EDM) method, and two end sides of each of the at least three gaps may extend in a direction perpendicular to the axial direction of the body, and centers of each of the gaps may be curved to form the at least three stoppers.

Two adjacent gaps may be separated in the axial direction of the body and are partially overlapped with each other in an azimuth angle direction, and both side portions of each of the gaps may be disposed in parallel to a side portion of another adjacent gap such that the elastic beam is formed between the two adjacent gaps.

The body may further include an opening formed at each of two end portions of each of the gaps.

The FBGs may be attached to the body across the stoppers.

The FBGs may be attached to the body across the elastic beam.

According to an aspect, a robot arm includes the force sensing apparatus described above.

The body of the force sensing apparatus is the same with a body of the robot arm.

The robot arm may further include grippers installed at an operational end of the body.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Reference will now be made in detail to embodiments, examples of which are illustrated in the accompanying drawings, wherein like reference numerals refer to like elements throughout, and the sizes of elements may be exaggerated for clarity and convenience of description. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Figure 1:
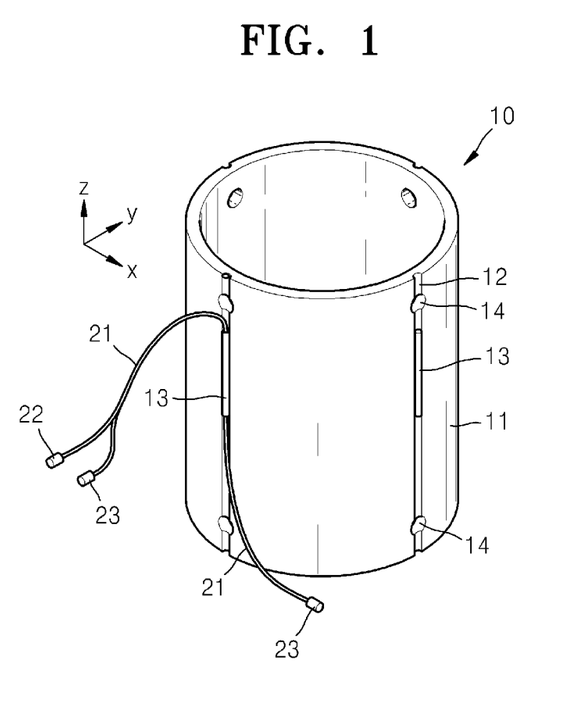
FIG. 1 is a schematic perspective view illustrating a structure of a force sensing apparatus according to an embodiment.

FIG. 1 is a schematic perspective view illustrating a structure of a force sensing apparatus 10 according to an embodiment. Referring to FIG. 1, the force sensing apparatus 10 may include a body 11 that has the form of a pipe and extends in an axial direction (i.e., a z-axis direction) and an optical fiber strain gauge attached to a surface of the body 11 to measure the degree of tension and compression of the body 11 in at least three directions. The body 11 may be formed of a material which may generate elastic deformation in response to even a small force. For example, the body 11 may be formed of a plastic material having a large degree of elastic deformation, such as polypropylene (PP). Also, although the body 11 has a cylindrical shape as illustrated in FIG. 1, the body 11 may also have a polygonal cylinder shape. In addition, bolt holes 14 may be formed in upper and lower portions of the body 11 in order to fix the body 11, such as to a robot arm, for example.

The optical fiber strain gauge measures a degree and direction of elastic deformation of the body 11. By measuring the degree and direction of elastic deformation of the body 11, an intensity and direction of a force acting upon the body 11 may be found. The optical fiber strain gauges may comprise, for example, at least three fiber Bragg gratings (FBGs) 13 that are attached to a surface of the body 11 and extend in an axial direction of the body 11, a light source 22 supplying light to each of the FBGs 13, and a light detector 23 that detects light reflected by each of the FBGs 13 or light that has passed through each of the FBGs 13. The FBGs 13 may be formed of thin optical fibers. Accordingly, in order to easily attach the FBGs 13 to the body 11, a groove 12 in which the FBGs 13 are safely mounted may be further formed in an axial direction in the surface of the body 11. The fact that the FBGs 13 extend along the axial direction of the body 11 does not mean that the FBGs 13 are necessarily parallel to the axial direction of the body 11, but may indicate that an arrangement direction of the FBGs 13 includes an axial direction component.

The FBGs 13 are formed by arranging gratings whose refractive indices periodically change inside an optical fiber. For example, the FBGs 13 may be formed by alternately and repeatedly arranging two different materials having different refractive indices in a core of an optical fiber. Due to the gratings, light of a predetermined wavelength from light that travels inside the FBGs 13 is reflected. A wavelength of the reflected light may vary according to an arrangement period of the gratings. When the FBGs 13 expand or shrink, the arrangement period of the gratings also expands or shrinks, and thus, the wavelength of reflected light varies. Accordingly, by measuring the wavelength of light reflected by the gratings at an input end of the FBGs 13 or by measuring a wavelength of light that passes through the FBGs 13 at an output end of the FBGs 13, a degree by which the FBGs 13 expand or shrink may be accurately measured. In addition, when the FBGs 13 are attached along the axial direction of the body 11, the FBGs 13 also expand or shrink according to a degree of tension or compression of the body 11. Thus, by measuring light reflected by or light that passed through the FBGs 13, the degree of tensioning or compression of the body 11 may be calculated.

The optical fiber strain gauges may further include a light transfer member 21 that transfers light emitted from the light source 22 to the FBGs 13 and transfers light output from the FBGs 13 to the light detector 23. The light transfer member 21 may be, for example, an optical fiber. The light source 22 and the light detector 23 may be not directly attached to the body 11 but may be connected to a user's computer or an exclusive calculation circuit (not shown), for example, via the light transfer member 21. Although the light detector 23 illustrated in FIG. 1 is disposed both at the input end and the output end of the FBGs 13, the light detector 23 may also be disposed only at one of the input end and the output end of the FBGs 13.

Figure 3A:
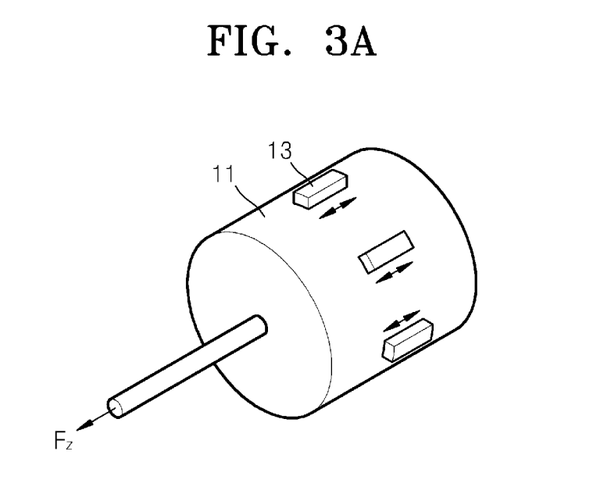
FIGS. 3A and 3B are schematic views illustrating an operational principle of the force sensing apparatuses illustrated in FIGS. 1 and 2.

To measure the degree of tension and compression of the body 11 in at least three directions, at least three FBGs 13 may be attached in at least three different positions on the surface of the body 11. In particular, in order to compensate for an error caused by temperature variation, for example, at least four FBGs 13 may be attached to the surface of the body 11. Although the light source 22 and the light detector 23 are illustrated as being connected to one FBG 13 in FIG. 3 for convenience of illustration, the light source 22 and the light detector 23 may also be arranged at each of the plurality of FBGs 13. According to the current embodiment, the plurality of FBGs 13 may be arranged at predetermined intervals in an azimuth angle direction. For example, when four FBGs 13 are used, the FBGs 13 may be arranged at intervals of 90 degrees along the azimuth angle direction.

Figure 2:
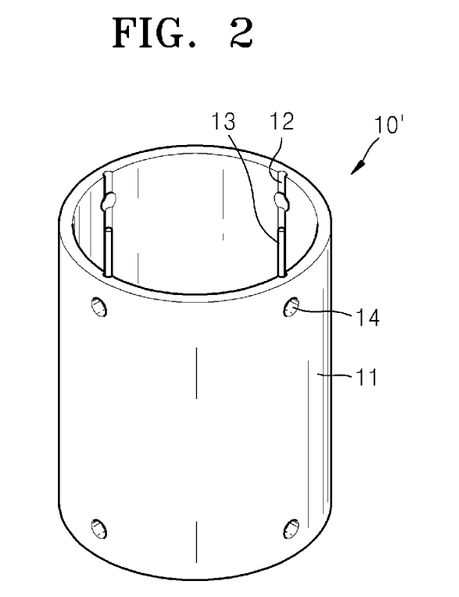
FIG. 2 is a schematic perspective view illustrating a structure of a force sensing apparatus according to an embodiment.

The FBGs 13 in FIG. 1 are illustrated as being attached to an outer surface of the body 11, but are not limited thereto. FIG. 2 is a schematic perspective view illustrating a structure of a force sensing apparatus 10' according to an embodiment, in which an FBG 13 is arranged on an inner surface of the body 11. As illustrated in FIG. 2, when the FBG 13 is arranged on the inner surface of the body 11, members such as a light transfer member 21, a light source 22, and a light detector 23 may be arranged in an inner space of the body 11. Also, a fine groove 12 may be formed in the inner surface of the body 11, and the FBG 13 may be safely mounted in an axial direction.

Figure 3B:
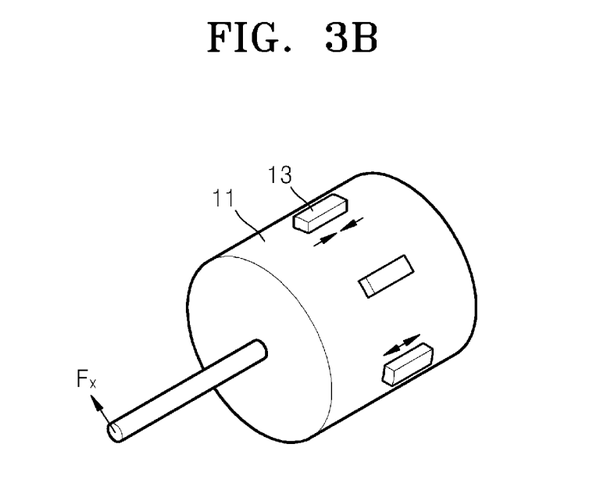

FIGS. 3A and 3B are schematic views illustrating an operational principle of the force sensing apparatuses 10 and 10' illustrated in FIGS. 1 and 2. First, as illustrated in FIG. 3A, when a force Fz acts upon the body 11 in an axial direction (z-axis direction), the body 11 is uniformly tensioned overall. Accordingly, all of the FBGs 13 attached to the body 11 expand. On the other hand, as illustrated in FIG. 3B, when a force Fx acts upon the body 11 in a direction perpendicular to the axial direction (e.g., x-axis direction), the body 11 bends in a direction in which the force acts. In this case, a portion of the body 11 on the side of bending is compressed, and a portion of the body 11 on the opposite side of the bent side is tensioned. Accordingly, the FBG 13 arranged on the side that bends shrinks, and the FBG 13 arranged on the opposite side expands. Thus, by measuring a degree by which the plurality of the FBGs 13 expand or shrink, a direction and intensity of force acting upon the body 11 may be calculated. The force sensing apparatuses 10 and 10' may be used in a force feedback system that measures a repulsive force of a living tissue or a force of a living tissue acting upon a surgical instrument when the living tissue comes into contact with the surgical instrument during an operation and that transfers the measured force to an operator (e.g., surgeon).

Figure 4:
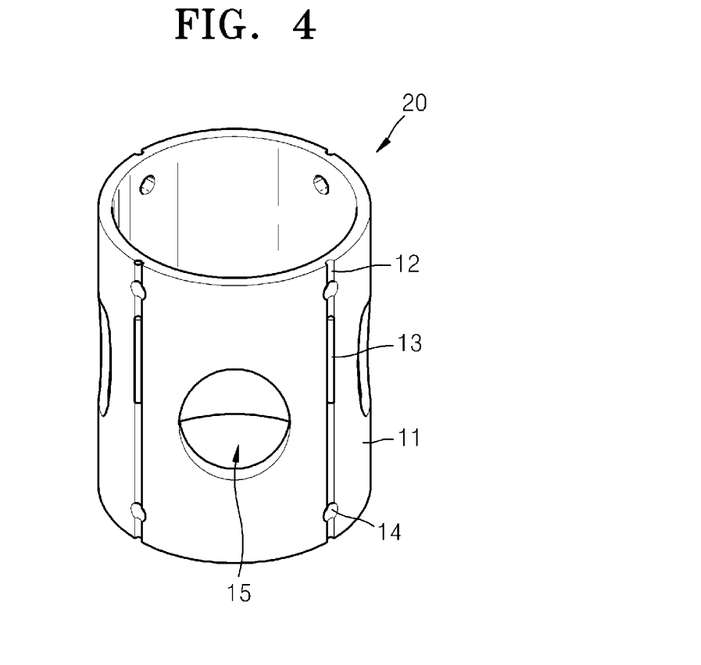
FIG. 4 is a schematic perspective view illustrating a structure of a force sensing apparatus according to an embodiment.

In order to increase the performance of the force sensing apparatus 10 and 10' (for example, resolution, measurement range, or error rate), the body 11 may have a large elastic deformation ratio and a small sensitivity difference according to a direction in which a force act upon the body 11. For example, when a difference between a sensitivity with respect to a force acting in the axial direction (z-axis direction) and a sensitivity with respect to a force acting in a direction perpendicular to the axial direction (x-axis direction or y-axis direction) is smaller, performance may increase. If the difference between sensitivities is large in each direction, an error in calculating the force may increase. FIG. 4 is a schematic perspective view illustrating a structure of a force sensing apparatus 20 according to an embodiment, which has been developed in consideration of the above point.

Referring to FIG. 4, the force sensing apparatus 20 includes a plurality of openings 15 that are respectively formed in the body 11 between each two adjacent FBGs 13. The rest of the configuration of the force sensing apparatus 20 illustrated in FIG. 4 is the same as the configuration of the force sensing apparatus 10 illustrated in FIG. 1. Referring to FIG. 4, the FBGs 13 are arranged on an outer surface of the body 11, but like in the embodiment of FIG. 2, the FBGs 13 may also be arranged on an inner surface of the body 11.

According to the current embodiment, characteristics of the force sensing apparatus 20 may vary according to a size and position of the openings 15. Accordingly, the performance of the force sensing apparatus 20 may be increased by adjusting the size and position of the openings 15 according to design purposes. In the embodiment of FIG. 4, if it is assumed that a force acts upon an upper end of the body 11, the FBGs 13 may preferably be arranged in a portion where most deformation of the body 11 occurs, and the openings 15 may be formed in a portion where least deformation of the body 11 occurs. As the openings 15 are formed, deformation occurring in other portions of the body 11 may be further increased. In addition, the openings 15 may be arranged such that a difference between deformation in the axial direction (for example, sensitivity in the z-axis direction) and deformation (for example, sensitivity in the x-axis direction or the y-axis direction) is minimized.

For example, the openings 15 may be arranged at an angle of 45 degrees from the bolt holes 14 respectively arranged in upper and lower portions of the body 11. That is, an extension line between a center of each of the bolt holes 14 and a center of each of the openings 15 may be inclined at 45 degrees from a horizontal plane. In this case, among spaces between each two adjacent openings 15, the largest deformation may occur in an upper portion of the body 11 upon which a force acts. Accordingly, the FBGs 13 may be arranged at upper portions of the body 11 between two adjacent openings 15. Also, the center of the openings 15 may be arranged at a position lower than a center of each of the FBGs 13 between two adjacent FBGs 13. The lower position is defined by assuming that an operational end of the force sensing apparatus 20 is the upper end of the body 11. The openings 15 may be arranged in respective spaces between the FBGs 13. For example, when four FBGs 13 are used, four openings 15 may be formed in the body 11. Thus, not only the sensitivity of the force sensing apparatus 20 may be increased, but also a difference in sensitivities for each direction may be minimized at the same time.

Figure 5:
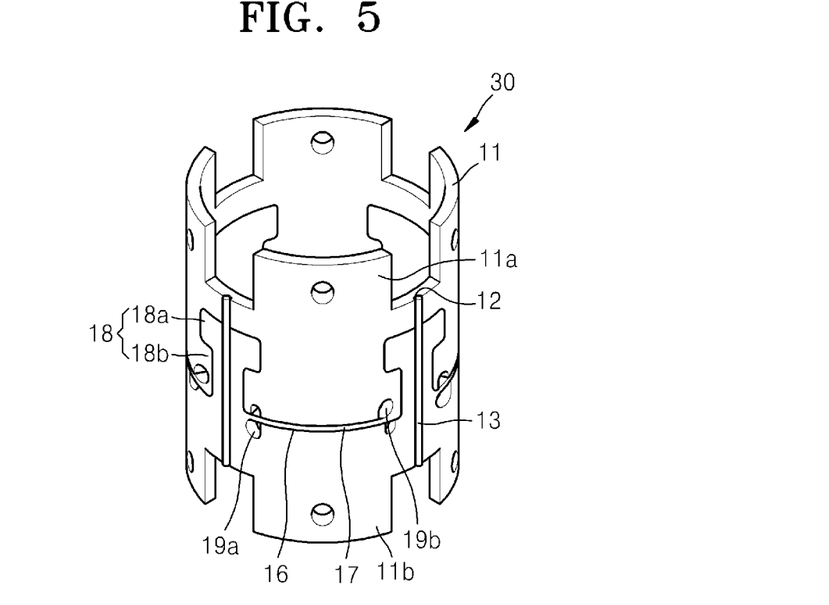
FIG. 5 is a schematic perspective view illustrating a structure of a force sensing apparatus according to an embodiment.
Figure 6:
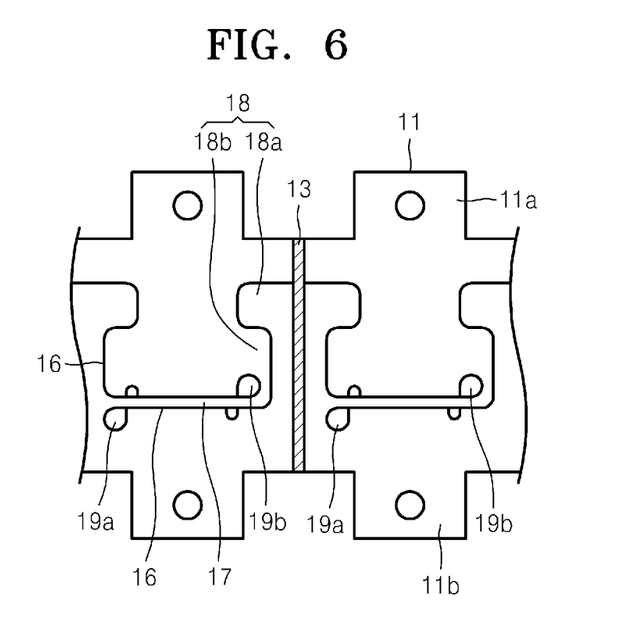
FIG. 6 is a partial development diagram of the force sensing apparatus illustrated in FIG. 5.

FIG. 5 is a schematic perspective view illustrating a structure of a force sensing apparatus 30 according to an embodiment. FIG. 6 is a partial development diagram of the force sensing apparatus 30 illustrated in FIG. 5. According to the embodiment of FIGS. 5 and 6, a thin elastic beam 17 which connects upper and lower portions of the body 15 is used instead of the openings 15 to improve the elastic deformation of the body 11.

Referring to FIGS. 5 and 6, the body 11 is divided into an upper portion 11a and a lower portion 11b that are separated from each other by a plurality of thin elastic beams 17 formed in a direction perpendicular to an axis. For example, a first end of each elastic beam 17 may be connected to the upper portion 11a of the body 11, and a second end of each elastic beam 17 may be connected to the lower portion 11b of the body 11. Gaps 16 are formed between the upper portion 11a of the body 11 and the elastic beam 17 and between the lower portion 11b of the body 11 and the elastic beam 17. The elastic beam 17, the upper portion 11a, and the lower portion 11b may be formed by partially cutting the single body 11, for example, by using a wire electrical discharge machining (wire EDM) method. The elastic beams 17 may be arranged in respective spaces between a plurality of FBGs 13. For example, when four FBGs 13 are used, four elastic beams 17 may be formed in the body 11.

Figure 7:
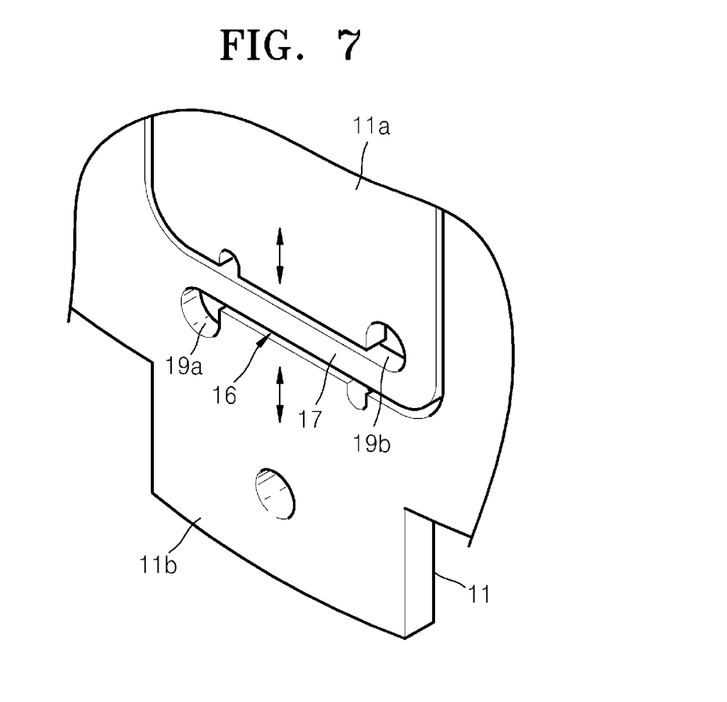
FIG. 7 is an expanded perspective view of an elastic beam of the force sensing apparatus illustrated in FIG. 5.

FIG. 7 is an expanded perspective view of the elastic beam 17 of the force sensing apparatus 30 illustrated in FIG. 5. Referring to FIG. 7, the body 11 includes the upper portion 11a, the elastic beam 17, and the lower portion 11b. In the embodiment of FIG. 7, a right end of the elastic beam 17 is connected to the upper portion 11a of the body 11, and a left end of the elastic beam 17 is connected to the lower portion 11b of the body 11. However, the embodiment of FIG. 7 is exemplary, and the right end of the elastic beam 17 may be connected to the lower portion 11b and the left end of the elastic beam 17 may be connected to the upper portion 11a. The gap 16 is formed between the upper portion 11a of the body 11 and the elastic beam 17 and between the lower portion 11b of the body 11 and the elastic beam 17 by cutting respective interspaces. Accordingly, when a force acts upon the body 11, the gap 16 between the elastic beam 17 and the lower portion 11a and the gap 16 between the elastic beam 17 and the upper portion 11b may easily enlarge, and thus, an elastic deformation of the body 11 may further increase. As a result, the sensitivity of the force sensing apparatus 30 may be further increased. Although the gap 16 is illustrated to be large in FIG. 7 for convenience, the gap 16 may be as small as approximately several dozens to several hundreds of μm. According to the current embodiment, to prevent the elastic beam 17 from being easily damaged, the body 11 may be formed of a metal having a good rigidity such as titanium (Ti), for example.

Meanwhile, the intensity of a force that may be supported by a typical force sensor may be reduced as the sensitivity of the force sensor is increased. Accordingly, if an excessive force acts upon the force sensor, the force sensor may be damaged, and measurement range of a force that may be measured by using the force sensor is reduced as the sensitivity of the force sensor is increased. To solve this problem, the force sensing apparatus 30 according to the current embodiment may further include a safety member that may generate a supporting force by itself or reduce the sensitivity thereof if a large external force that is outside a measurement range acts upon the force sensing apparatus 30.

For example, referring to FIGS. 5 and 6 again, a stopper 18 for preventing excessive deformation of the elastic beam 17 may be formed between two adjacent elastic beams 17. The stopper 18 may be formed of the upper portion 11a and the lower portion 11b of the body 11 that is divided by the gap 16. For example, the stopper 18 may be formed of a first protrusion 18a that is protruded and extended from the lower portion 11b toward the upper portion 11a in the axis direction and a second protrusion 18b that is protruded and extended from the upper portion 11a toward the lower portion 11b in the axis direction to surround the first protrusion 18a of the lower portion 11b. The first protrusion 18a of the lower portion 11b may have an intermediate portion having a relatively small width and an end portion having a relatively large width, and the second protrusion 18b of the upper portion 11a may also have an intermediate portion having a relatively small width and an end portion having a relatively large width. That is, the first protrusion 18a of the lower portion 11b and the second protrusion 18b of the upper portion 11a may be formed in a complementary engagement.

Figure 8:
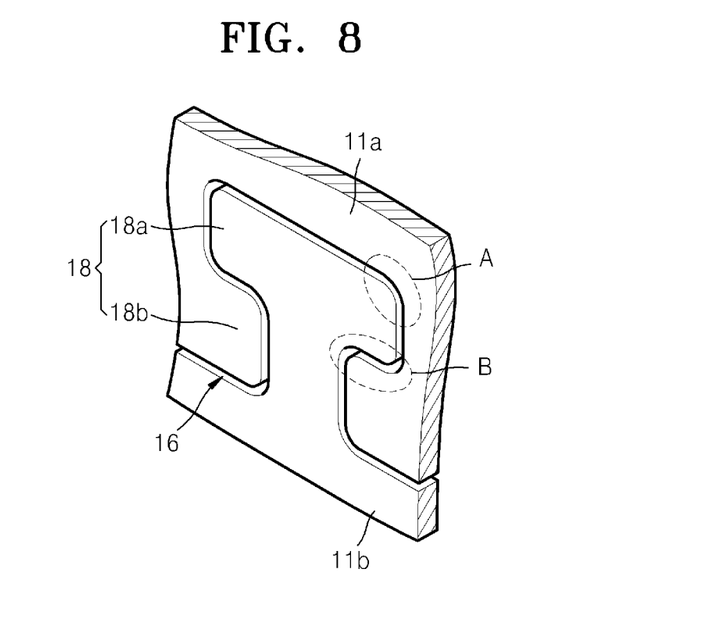
FIG. 8 is an expanded perspective view illustrating a stopper of the force sensing apparatus illustrated in FIG. 5.

FIG. 8 is an expanded perspective view illustrating the stopper 18 of the force sensing apparatus 30 illustrated in FIG. 5. Referring to FIG. 8, the body 11 is divided into the upper portion 11a and the lower portion 11b by the gap 16 that is bent in a form such as 'Ω', for example. Due to the gap 16 having the form described above, the upper portion 11a and the lower portion 11b have the second protrusion 18b and the first protrusion 18a in a complementary form, respectively. The first protrusion 18a and the second protrusion 18b are formed to be engaged with each other, thereby functioning as the stopper 18 that may prevent excessive deformation of the elastic beam 17.

For example, when the upper portion 11a of the body 11 is acted upon by a large force in a +z direction, the first protrusion 18a and the second protrusion 18b contact each other in a portion B marked in FIG. 8. Then, movement of the upper portion 11a in the +z direction is limited. Also, when the upper portion 11a of the body 11 is acted upon by a large force in a −z direction, the first protrusion 18a and the second protrusion 18b contact each other in a portion A marked in FIG. 8. Then, movement of the upper portion 11a in the −z direction is limited. Once the first protrusion 18a and the second protrusion 18b contact each other, the first and second protrusions 18a and 18b may support an external force working on the body 11. Accordingly, even when a large force above the measurement range of the force sensing apparatus 30 acts upon the body 11, the stopper 18 may prevent the elastic beam 17 from deforming outside a range in which it may be elastically restored. Accordingly, damage to the force sensing apparatus 30 may be prevented.

Figure 9:
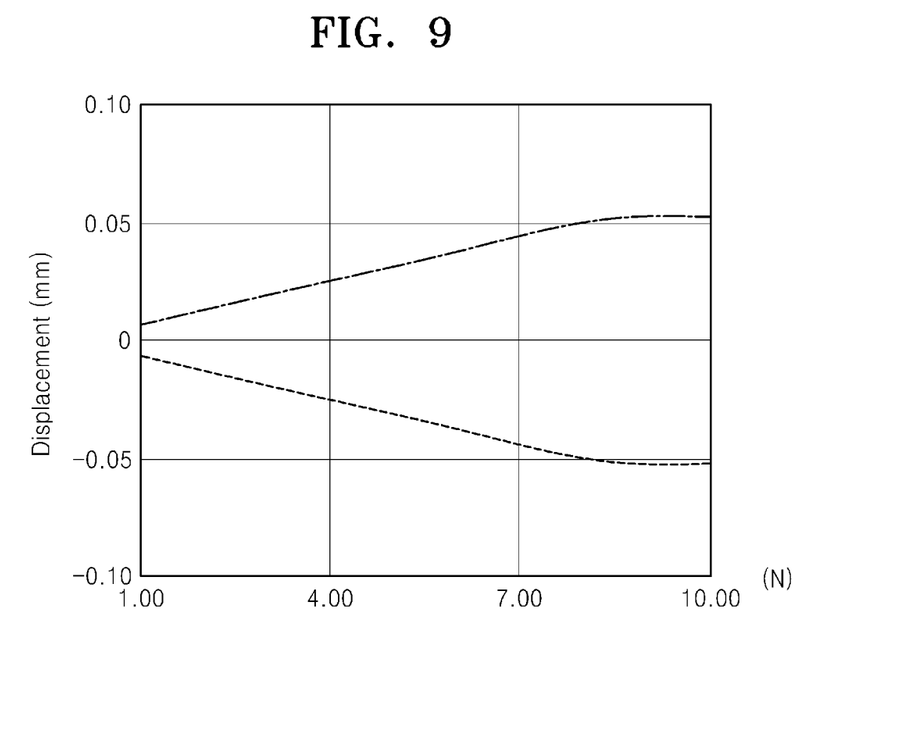
FIG. 9 is a graph showing a displacement amount of a body of the force sensing apparatus of FIG. 5 when a force works on the body.

FIG. 9 is a graph showing a displacement amount of the body 11 of the force sensing apparatus 30 of FIG. 5 when a force acts upon the body 11. A horizontal axis in FIG. 9 denotes an intensity of a force N, and a vertical axis denotes a relative displacement of the upper portion 11a and the lower portion 11b of the body 11. Also, a slope of the graph may be proportional to the sensitivity of the force sensing apparatus 30, and signs of the slope may be opposite to each other according to a direction in which the force N acts. Referring to FIG. 9, when a force of at least 8N is applied to the body 11, the slope of the graph varies as the first and second protrusions 18a and 18b contact each other. As illustrated in FIG. 9, even after the first and second protrusions 18a and 18b contact each other, the slope of the graph does not become completely zero. Accordingly, a double mode in which the sensitivity of force sensing varies before and after the contact between the first and second protrusions 18a and 18b may be measured. Accordingly, according to the current embodiment, forces in a relatively wide range may be measured and durability of the force sensing apparatus 30 may be improved.

The plurality of elastic beams 17 and the stopper 18 described above may be formed in a monolithic manner by forming a plurality of gaps 16 in the single body 11 by using, for example, a wire EDM method. Referring to FIG. 6 again, both side portions of each gap 16 are formed in a direction perpendicular to an axis, and a center portion of the gap 16 is curved in a form of 'Ω' so as to form the stopper 18. Two adjacent gaps 16 are separated from each other in the axis direction and are partially overlapped with each other in an azimuth angle direction. Also, the both side portions of the gap 16 extended in a direction perpendicular to an axis of the body 11 are arranged parallel to a side portion of another gap 16, and thus the elastic beam 17 may be formed between the two parallel gaps 16.

According to the embodiment of FIG. 6, a left side portion of the gap 16 is disposed between the lower portion of the body 11 and the elastic beam 17, and a right side portion of the gap 16 is disposed between the upper portion 11a of the body 11 and the elastic beam 17. That is, the gap 16 starts from between the lower portion 11b of the body 11 and one elastic beam 17 and passes through the stopper 18 to be extended up to a portion between the upper portion 11a of the body 11 and another elastic beam 17. If four elastic beams 17 and four stoppers 18 are to be formed, four gaps 16 may be formed in the body 11. Openings 19a and 19b may be formed at two end portions of each of the gaps 16 to prevent the body 11 from failing due to fatigue caused while the body 11 is repeatedly elastically deformed. Meanwhile, the FBG 13 illustrated in FIG. 6 to be disposed across the stopper 18 is exemplary, and the FBG 13 may also be attached across the elastic beam 17. Also, according to the current embodiment, the FBG 13 may be attached to an inner surface of the body 11 as in the embodiment of FIG. 2.

The force sensing apparatuses 10, 10', 20, and 30 according to the embodiments are employed in a robot arm of a surgery robot or the like to find out whether the robot arm contacts a living tissue or other objects and to measure a repulsive force of the objects or forces applied to the objects due to a particular contact. In particular, the force sensing apparatuses 10, 10', 20, and 30 use an optical fiber strain gauge, and thus, may measure a force without being affected by an electromagnetic field. Also, the force sensing apparatuses 10, 10', 20, and 30 may be manufactured to have a small size so as to be disposed as close as possible to an operational end of a robot, such as an end of a surgery arm of a surgery robot, for example, thereby accurately measuring a force acting upon the operational end.

Figure 10:
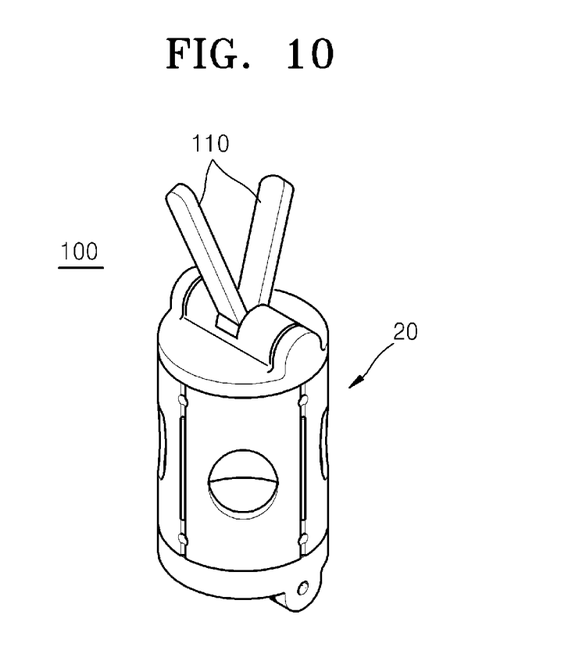
FIG. 10 is a perspective view illustrating a robot arm including the force sensing apparatus of FIG. 4.
Figure 11:
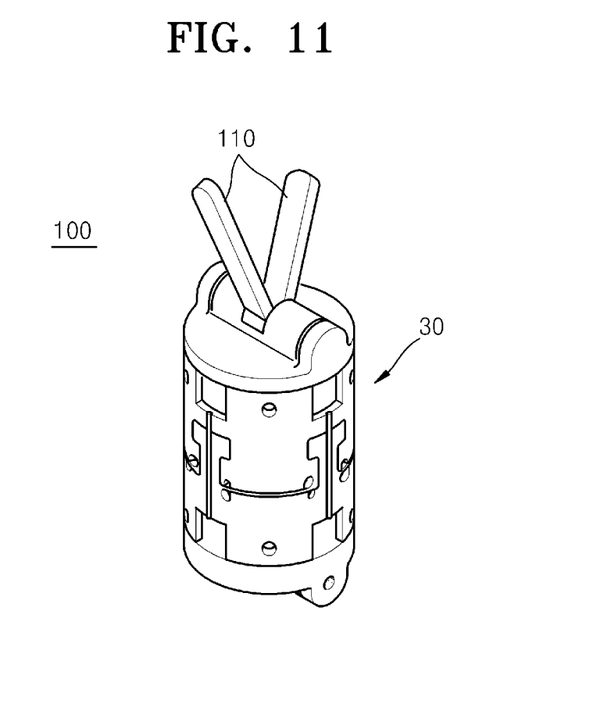
FIG. 11 is a perspective view illustrating a robot arm including the force sensing apparatus of FIG. 5.

FIG. 10 is a perspective view illustrating a robot arm 100 including the force sensing apparatus 20 of FIG. 4. FIG. 11 is a perspective view illustrating a robot arm 100 including the force sensing apparatus 30 of FIG. 5. Referring to FIGS. 10 and 11, a body of the robot arm 100 may be the same with the body 11 of the force sensing apparatuses 20 and 30, and for example, gripper 110 for holding a surgical instrument or other objects may be installed at an operational end of the body 11. Although not illustrated in the drawings, a lower portion of the robot arm 100 may be coupled to another joint portion of a robot. The force sensing apparatuses 20 and 30 may measure force acting between a surgical instrument picked up by the gripper 110 and a living tissue, and may return the value of the measured force to an operator of a surgery robot.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A force sensing apparatus, comprising:
   a body that is elastically deformable and has a pipe form extending along an axial direction of the body;
   at least three fiber Bragg gratings (FBGs) attached to a surface of the body;
   an opening in the body between each two adjacent FBGs so that a plane perpendicular to the axial direction of the body intersects the opening and the two adjacent FBGs;
   a light source configured to provide light to each of the FBGs; and
   a light detector configured to detect light reflected by each of the FBGs or light that has passed through each of the FBGs.

2. The force sensing apparatus of claim 1, wherein the at least three FBGs are arranged to extend along the axial direction of the body.

3. The force sensing apparatus of claim 1, wherein the at least three FBGs are attached to the surface of the body at at least three different positions at predetermined intervals along an azimuth angle direction.

4. The force sensing apparatus of claim 1, wherein the FBGs are attached to an external surface or an inner surface of the body.

5. The force sensing apparatus of claim 1, wherein the body comprises plastic material.

6. The force sensing apparatus of claim 1, further comprising:
   a plurality of bolt holes in an upper portion and a lower portion of the body;
   wherein an extension line between a center of two adjacent bolt holes and a center of the opening is at a 45-degree angle with respect to a horizontal surface.

7. The force sensing apparatus of claim 1, wherein when an operational end of the force sensing apparatus is assumed to be an upper portion of the body, a center of the opening is at a position lower than a center of two adjacent FBGs.

8. A force sensing apparatus comprising:
   a body that is elastically deformable and has a pipe form extending along an axial direction of the body;
   at least three fiber Bragg gratings (FBGs) attached to a surface of the body;
   a light source configured to provide light to each of the FBGs; and
   a light detector configured to detect light reflected by each of the FBGs or light that has passed through each of the FBGs;
   wherein the body comprises:
      an upper portion and a lower portion separated from each other;
      at least three elastic beams that connect the upper portion and the lower portion of the body and are extended in a direction perpendicular to an axis of the body;
      gaps between one of the elastic beams and the upper portion of the body and between one of the elastic beams and the lower portion of the body; and
      a stopper between each two adjacent elastic beams so that a plane perpendicular to the axial direction of the body intersects the stopper and one of the at least three FBGs between the two adjacent elastic beams.

9. The force sensing apparatus of claim 8, wherein the body comprises metal.

10. The force sensing apparatus of claim 8, wherein a first end portion of the elastic beams is connected to the upper portion of the body, and
   wherein a second end portion of the elastic beams opposite to the first end portion is connected to the lower portion of the body.

11. The force sensing apparatus of claim 8, wherein the stopper comprises:
   a first protrusion that protrudes and extends from the lower portion of the body toward the upper portion of the body in the axial direction of the body; and
   a second protrusion that protrudes and extends from the upper portion of the body toward the lower portion of the body in the axial direction of the body to surround the first protrusion.

12. The force sensing apparatus of claim 11, wherein the first protrusion comprises an intermediate portion having a first width and an end portion having a second width,
wherein the second protrusion comprises an intermediate portion having a third width and an end portion having a fourth width,
wherein the first protrusion and the second protrusion are engaged with each other in a complementary form,
wherein the first width is smaller than the second width, and
wherein the third width is smaller than the fourth width.

13. The force sensing apparatus of claim 12, wherein the gaps extend between the first protrusion and the second protrusion.

14. The force sensing apparatus of claim 11, wherein the at least three elastic beams and the stopper between each two adjacent elastic beams are formed in a monolithic manner by forming at least three gaps in the body by using a wire electrical discharge machining (EDM) method,
wherein two end sides of each of the at least three gaps extend in a direction perpendicular to the axial direction of the body, and
wherein centers of each of the gaps are curved to form the stopper between each two adjacent elastic beams.

15. The force sensing apparatus of claim 14, wherein two adjacent gaps of the at least three gaps are separated in the axial direction of the body and are partially overlapped with each other in an azimuth angle direction, and
wherein both side portions of each of the two adjacent gaps are in parallel to a side portion of another one of the two adjacent gaps such that a respective one of the at least three elastic beams is between the two adjacent gaps.

16. The force sensing apparatus of claim 14, wherein the body further comprises an opening at each of two end portions of each of the gaps.

17. The force sensing apparatus of claim 8, wherein one of the FBGs is attached to the body across the stopper between each two adjacent elastic beams.

18. The force sensing apparatus of claim 8, wherein the FBGs are attached to the body across the elastic beams.

19. A robot arm, comprising:
a body that is elastically deformable and has a pipe form extending along an axial direction of the body;
at least three fiber Bragg gratings (FBGs) attached to a surface of the body;
an opening in the body between each two adjacent FBGs so that a plane perpendicular to the axial direction of the body intersects the opening and the two adjacent FBGs;
a light source configured to provide light to each of the FBGs; and
a light detector configured to detect light reflected by each of the FBGs or light that has passed through each of the FBGs.

20. The robot arm of claim 19, wherein the body of the force sensing apparatus is the same with a body of the robot arm.

21. The robot arm of claim 19, further comprising grippers installed at an operational end of the body.

22. A method to sense a force applied to an elastically deformable body, the method comprising:
attaching at least three optical fiber strain gauges to the body;
forming an opening in the body between two adjacent optical fiber strain gauges of the at least three optical fiber strain gauges so that a plane perpendicular to an axial direction of the elastically deformable body intersects the opening and the two adjacent optical fiber strain gauges;
providing light to each of the at least three optical fiber strain gauges;
detecting the light from each of the at least three optical fiber strain gauges; and
calculating the force applied to the body based on the detected light.

* * * * *